United States Patent
Sinha

[11] Patent Number: 6,053,041
[45] Date of Patent: *Apr. 25, 2000

[54] NONINVASIVE METHOD FOR DETERMINING THE LIQUID LEVEL AND DENSITY INSIDE OF A CONTAINER

[75] Inventor: Dipen N. Sinha, Los Alamos, N.Mex.

[73] Assignee: The Regents of the University of California, Los Alamos, N.Mex.

[*] Notice: This patent issued on a continued prosecution application filed under 37 CFR 1.53(d), and is subject to the twenty year patent term provisions of 35 U.S.C. 154(a)(2).

[21] Appl. No.: 08/395,932

[22] Filed: Feb. 27, 1995

[51] Int. Cl.[7] .............................. G01F 23/28; G08B 21/00
[52] U.S. Cl. ...................... 73/290 V; 340/621; 367/908
[58] Field of Search ................ 73/290 V, 32 A; 340/618, 621; 367/908

[56] References Cited

U.S. PATENT DOCUMENTS

| | | | |
|---|---|---|---|
| 4,213,337 | 7/1980 | Langdon | 73/290 V |
| 4,240,285 | 12/1980 | Langdon | 73/32 A |
| 4,248,087 | 2/1981 | Dennis et al. | 73/290 V |
| 4,383,443 | 5/1983 | Langdon | 73/290 V |
| 4,841,256 | 6/1989 | Gastgeb | 340/621 X |
| 5,015,995 | 5/1991 | Holroyd | 340/621 |
| 5,031,451 | 7/1991 | Webster | 73/290 V |
| 5,074,148 | 12/1991 | Lew | 73/290 V |
| 5,264,831 | 11/1993 | Pfeiffer | 340/621 |

FOREIGN PATENT DOCUMENTS

| | | | |
|---|---|---|---|
| 6118 | 1/1981 | Japan | 73/290 V |
| 723431 | 3/1980 | U.S.S.R. | 73/32 A |
| 1250910 | 8/1986 | U.S.S.R. | 73/32 A |

OTHER PUBLICATIONS

R.M. Langdon, "Vibratory Process Control Transducers," Electronic Engineering, pp. 159–168 (Nov. 1981).

*Primary Examiner*—Hezron Williams
*Assistant Examiner*—Willie Morris Worth
*Attorney, Agent, or Firm*—Samuel M. Freund

[57] ABSTRACT

Noninvasive method for determining the liquid level and density inside of a container having arbitrary dimension and shape. By generating a flexural acoustic wave in the container shell and measuring the phase difference of the detected flexural wave from that of the originally generated wave a small distance from the generated wave, while moving the generation and detection means through the liquid/vapor interface, this interface can be detected. Both the wave generation and wave detection may be achieved by transducers on the surface of the container. A change in the phase difference over the outer surface of the vessel signifies that a liquid/vapor interface has been crossed, while the magnitude of the phase difference can be related to fluid density immediately opposite the measurement position on the surface of the vessel.

6 Claims, 6 Drawing Sheets

NONINVASIVE METHOD FOR DETERMINING THE LIQUID LEVEL AND DENSITY INSIDE OF A CONTAINER

FIELD OF THE INVENTION

The present invention relates generally to the measurement of liquid level and density in containers and, more particularly, to the determination of changes in the propagation velocity of sound in the walls of a container as a result of the presence of a fluid. The invention was made with government support under Contract No. W-7405-ENG-36 awarded by the U.S. Department of Energy and the Regents of the University of California. The government has certain rights in the invention.

BACKGROUND OF THE INVENTION

It is often necessary to noninvasively determine various physical characteristics of the fluid contents inside sealed containers such as drums, reactor vessels, railroad tanker cars, holding tanks, and the like. Typically the information required consists of fill level and liquid density. As an example, there are hundreds of thousands of 55-gallon drums at various locations in the United States which are filled with hazardous waste materials, and other bulk containers contain chemical (weapons) nerve agents. In many cases, records as to the nature of the contents have been lost or destroyed. These drums are often stacked on top of one another in several rows and can be accessed only from the side of the container for testing. Prior to disposal, it is important to obtain an idea as to the liquid level and density. Another example includes the maintenance of current inventories of chemical-filled railroad tanker cars in order for the chemical industry to control customer shipments. Additionally, there is a need for liquid level monitoring in reactor vessels for accurate process control.

There are numerous liquid level measuring devices currently available. However, most of these devices require invasion of the containing vessel by placing sensors therein or by arranging for windows through which observations may be made. For example, in R. M. Langdon, "Vibratory Process Control Transducers," Electronic Engineering, pages 159–168 (November 1981), the authors disclose that flexural vibration of metal structures inserted into liquids exhibits vibrational frequencies dependent upon liquid level. A rigid metal rod or tube of suitable cross section is inserted into the liquid with a piezoelectric or electromagnetic transducer attached to it to generate flexural vibrations at frequencies in the kilohertz range. The speed with which the vibrations pass along the rod is constant for a given frequency and depends on such things as the density and elastic constants of the metal and the rod dimensions. It also depends on the nature of the material surrounding the rod so that when the rod is immersed in a liquid, a significant reduction in rod-wave velocity occurs. Consequently, when the rod is mounted in such a way that it can resonate in a flexural mode, the transit time of waves passing along the rod and hence the frequency of vibration is reduced by immersion in a liquid. The change in resonant frequency is approximately linearly dependent on the fraction of the rod immersed so this frequency provides a measure of liquid level. A similar device is described in Hyok S. Lew, "Resonance Frequency Liquid Level Sensor," U.S. Pat. No. 5,074, 148, which issued on Dec. 24, 1991.

Another widely used ultrasonic technique for fill-level monitoring in containers is echo-ranging. The most common adaptation of this technique employs an air transducer to direct a beam of ultrasound through the air above the surface of the liquid downward to the liquid surface. The reflected ultrasonic signal is detected either by the same transducer or by a second transducer, the propagation time through the air space providing a direct and continuous measure of the fill level in the container. This invasive approach cannot be used for sealed containers unless the transducers in the air space directly above the liquid surface are placed there before the liquid is introduced to the container, since an ultrasonic wave cannot be adequately coupled into the air in the container from outside thereof. Unless complex reference subtraction techniques are employed, the accuracy of the technique suffers from the fact that the sound velocity in the medium above the liquid whose level is to be determined varies with temperature and composition of the gas therein.

If the liquid has a fixed composition, the pulse-echo sensor may be mounted at the bottom of the container and outside of it. A signal may be generated in the liquid through the container wall for continuous fill-level monitoring using the return propagation time through the liquid to the liquid/vapor interface. A difficulty with this method arises if the bottom of the drum cannot be readily accessed. Moreover, sound speed is affected by liquid temperature, and highly attenuating liquids or long pathlengths may completely absorb the signal. Additionally, the presence of bubbles or other suspended particles will prevent the signal from entering the bulk of the liquid because of sound scattering. Contamination of the liquid by impurities, liquid stratification, and poor coupling of transducers to the container surface will all adversely affect such measurements.

A variation of this noninvasive ultrasonic technique introduces pulsed ultrasonic waves into a vessel at various levels through the side of the container and observes the echo from the opposite side of the container. When the liquid level is exceeded, there is no return signal or echo. The ultrasonic pulse is introduced into the container using a transducer attached to the surface thereof using a coupling gel or some other coupling means. Below the liquid level, the pulse propagates through the liquid, bounces off of the other side of the container and is detected by the same transducer. Again, the return signal may be severely attenuated in the situation where the liquid is strongly absorbing at the frequency employed or has substantial numbers of suspended particles which are effective in scattering sound. A similar effect occurs when the container is very large.

Other noninvasive techniques include nuclear or x-ray imaging which are expensive, nonportable, and complex.

For sealed containers, such as chemical storage drums, then, there does not appear to be a reliable way to determine liquid level and density of the contents without opening them.

Accordingly, it is an object of the present invention to provide an accurate, noninvasive method for measuring the fill level of liquids in containers.

Another object of the invention is to provide an accurate, noninvasive method for measuring the fill level of liquids in containers independent of the size and shape thereof.

Yet another object of the present invention is to provide an accurate, noninvasive method for measuring the density of liquids in containers.

Still another object of the invention is to provide an accurate, noninvasive method for measuring the density of liquids in containers independent of the size and shape thereof.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for determining the liquid level in a container includes the steps of introducing a burst of sound having a chosen frequency into the shell of the container at a chosen distance from the bottom thereof, establishing thereby a flexural wave therein, detecting the magnitude of the flexural wave generated in the shell at a point thereon nearby to the point of introduction of the burst of sound in a direction therefrom which is substantially parallel to the surface of the liquid, and measuring the phase difference between the burst of sound and the detected flexural wave; whereby the liquid level may be determined by monitoring the magnitude of the phase difference and observing a change therein.

Preferably, the present method further includes the step of moving the location of introduction of the burst of sound and the measurement of the magnitude of the flexural wave produced thereby either up or down from the chosen distance from the bottom of the container.

In another aspect of the present invention, in accordance with its objects and purposes, a method for determining the density of a liquid in a container is also described, the method including the steps of introducing a burst of sound having a chosen frequency into the shell of the container at a point thereon the interior of which contacts the liquid under investigation, establishing thereby a flexural wave therein, detecting the magnitude of the flexural wave generated in the shell at a point on the shell nearby to the point of introduction of the burst of sound, and measuring the phase difference between the burst of sound and the detected flexural wave, whereby the liquid density is obtained from the magnitude of the phase difference.

In yet another aspect of the present invention, in accordance with its objects and purposes, a method for continuously determining the level of a liquid in a container comprising the steps of introducing a burst of sound having a chosen frequency into the wall of the container at a chosen distance from the bottom thereof, establishing thereby a flexural wave therein, detecting the magnitude of the flexural wave generated in the wall at a point thereon nearby to the point of introduction of the burst of sound in a direction therefrom which is substantially perpendicular to the surface of the liquid and on the other side thereof from the location of the introduction of the burst of sound into the wall of the container, and measuring the phase difference between the burst of sound and the detected flexural wave; whereby the liquid level may be determined by monitoring the magnitude of the phase difference.

Benefits and advantages of the invention include the noninvasive nature of the measurements and independence of the measurements from container size and shape, independence of completeness of coupling between the container wall and transducers, and independence from attenuation by the liquid contained in the vessel or other liquid conditions such as the presence of bubbles and particulates. Additionally, simultaneous liquid density measurements may be obtained with a resolution of better than 0.01 g/cm$^3$.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings.

DETAILED DESCRIPTION

Briefly, the present invention includes the noninvasive measurement of liquid level and density in containers of arbitrary size and shape by generating a flexural acoustic wave in the container shell and measuring the phase difference of the detected flexural wave from that of the originally generated wave, a small distance from the generated wave. Both the wave generation and wave detection may be achieved by transducers on the surface of the container. A change in the phase difference over the outer surface of the vessel signifies that a liquid/vapor interface has been crossed, while the magnitude of the phase difference can be related to fluid density immediately opposite the measurement position on the surface of the vessel.

It is well known that sound may propagate through a metal plate or other elastic or stiff material in the form of flexural or bending waves. The speed, $C_b$, of the bending wave depends upon the thickness, t, and the frequency, f, according to the relationship:

$$C_b = \sqrt{1.8 t f C_m}, \qquad (1)$$

where $C_m$ is the speed of longitudinal waves in the metal. This is also the speed of sound in the bulk metal. The bending waves slow when the plate comes in contact with a liquid. The relationship between the wavelength, $\lambda$, and the frequency become dependent on the liquid density according to the relationship:

$$\omega^2 = \frac{Dk^5}{(\rho_L + tk\rho_m)}, \quad (2)$$

where $\omega=2\pi f$ is the angular frequency, $k=2\pi\lambda$ is the wavenumber, D is the rigidity modulus, and $\rho_L$ and $\rho_m$ are the liquid density and metal plate density, respectively. Equation 2 is a nonlinear equation with respect to applied frequency. However, a simpler, but less accurate, form of this equation is the following:

$$C_b = \left(\frac{\omega^3 D}{\rho_L}\right)^{1/5}. \quad (3)$$

This equation shows the relationship between the sound propagation speed and the density of the liquid and the impressed frequency. Clearly, the higher the liquid density, the slower sound waves are propagated in the metal. A metal container, such as a 55-gallon drum, can be considered as a rolled metal sheet. Equations 1–3 are obeyed for any bending waves excited in the drum.

Figure 1:
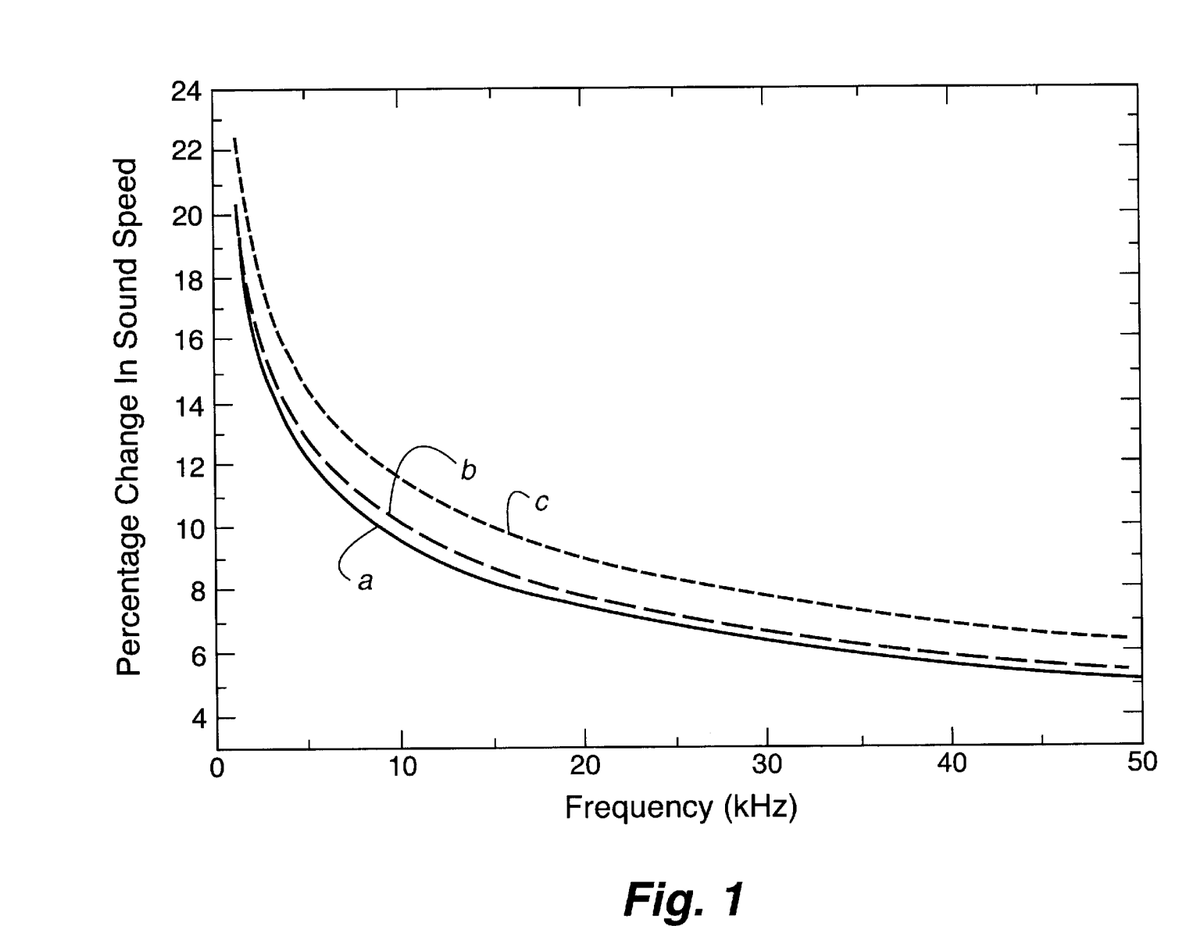
FIGS. 1a–c contrast the calculated percentage decrease in the speed of propagation of flexural waves in the wall of the drum as a function of frequency for liquids having various densities, as compared with that for an empty drum; (a) being water having a density of 1.00, (b) being GA (a chemical nerve agent) having a density of 1.07 and (c) being mustard (also a chemical nerve agent) having a density of 1.3.

Turning now to the drawings, FIGS. 1a–c illustrate the calculated percentage decrease in the propagation speed of bending waves in the container wall below the liquid level for liquids having different densities and contained in a 55-gallon drum, as a function of frequency when compared with an empty drum; (a) is water having a density of 1.00, (b) is GA (a chemical nerve agent) having a density of 1.07, while (c) is mustard (a chemical nerve agent) having a density of 1.3. Clearly, the effect is dependent upon density of the liquid in contact with the container wall and is greater for greater density liquids.

Figure 2:
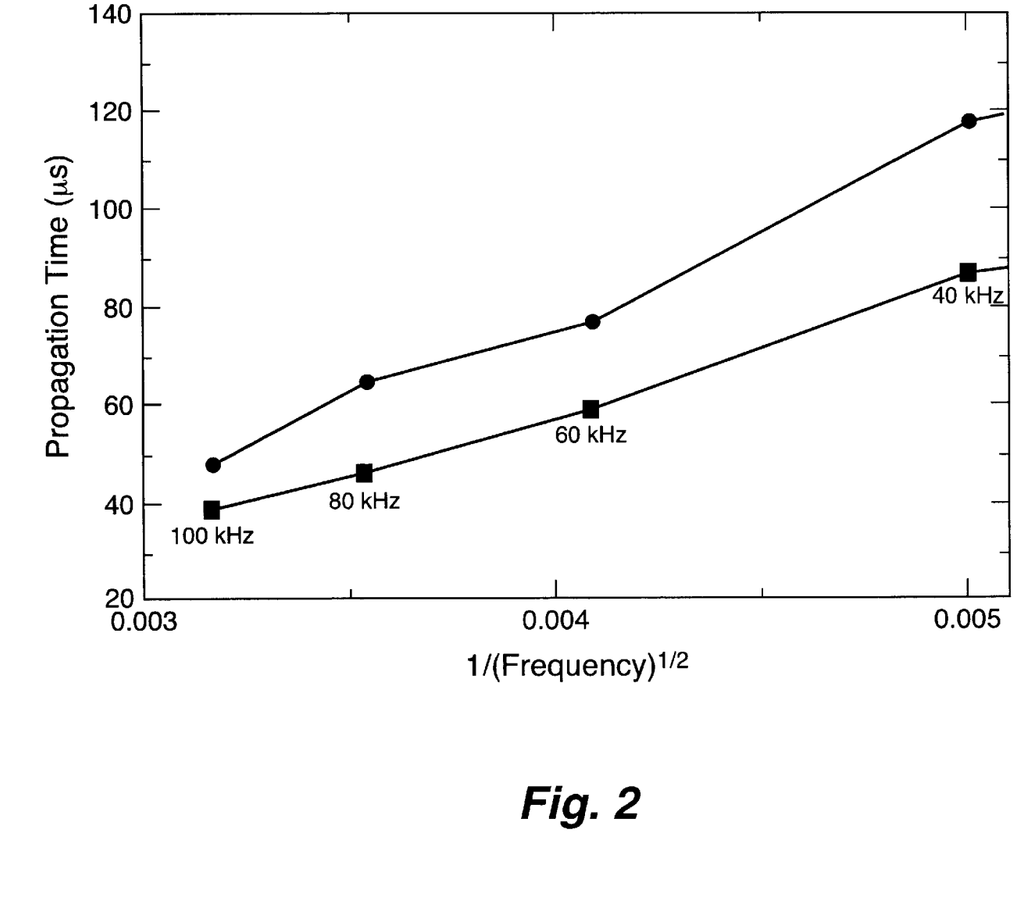
FIG. 2 illustrates the analytical form of the speed of propagation of a bending wave in a metal sheet as a function of the inverse square-root of the frequency when the sheet is in contact with air (square symbols) and water (circular symbols), both transducers being either above the liquid or below the liquid, respectively.

In FIG. 2, experimental data for the sound propagation time for bending waves versus the inverse of the square root of the frequency are plotted for a metal container wall backed either by air (squares) or by water (circles). The bending waves were induced between two fixed transducers (7.5 cm apart) in the 0.25 mm thick wall at four pure frequencies (tone bursts). Both curves follow Equations 1–3, hereinabove, and it is clear that higher fluid density results in longer sound propagation times, as stated above, at all frequencies measured. The effect takes place primarily at the liquid interface and is effectively unrelated to the speed of sound in the fluid itself. Thus, if one measures the bending wave propagation in a region above the liquid/gas interface, and again below this interface, one would observe a decrease in the propagation speed. Detection of this change in the speed of the bending wave propagation constitutes the underlying principle of the present method. Also illustrated in FIG. 1, the magnitude of the effect of the presence of liquids decreases monotonically with increasing frequency. Therefore, small changes in propagation time of a low-frequency flexural wave must be measured. Standard time-of-flight measurements (e.g., echo-ranging using pulses) require sharply defined pulses in order that small time shifts can be detected. However, generation of sharply-defined pulses demands a significant high-frequency component of the pulse packet. Since the flexural waves are frequency dependent, different frequencies propagate with different speeds (higher frequencies traveling faster than lower frequencies), thereby distorting the pulse as it propagates. This renders inaccurate measurements of small time differences. Additionally, if one utilizes pulses only having low frequency components, it is also difficult to accurately observe small shifts in time. By using a tone burst having a single frequency, however, one can readily determine the time differences using phase-difference measurements. Moreover, electronic circuitry for phase measurements is inexpensive and widely available. Applied frequency is selected for a chosen container type (in particular, wall thickness and type) in order to maximize the observed phase shift (in going from air-backed to liquid-backed propagation), while keeping this shift below 360°. For simple liquid-level measurements, the frequency need not be optimized since one is observing a sudden phase change. However, for liquid-density measurements, greater accuracy can be obtained where the effect is maximized. The maximization procedure need only be carried out once for a given container type.

Having generally described the method of the present invention, the following Examples are presented to more specifically illustrate its applications.

EXAMPLE 1

Figure 3:
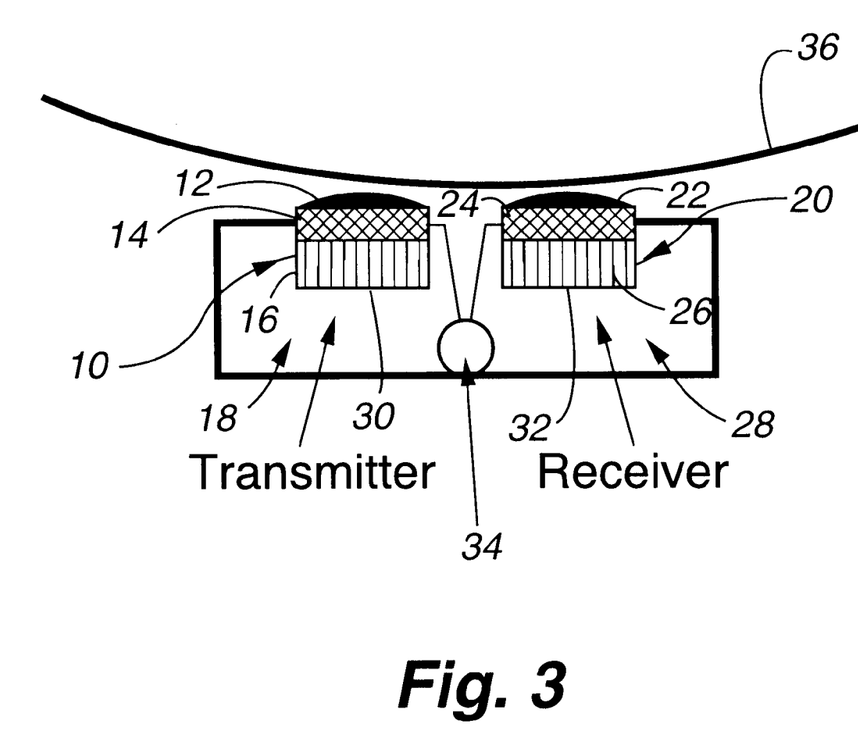
FIG. 3 is a schematic representation of the top view of an apparatus used to practice the method of the present invention illustrating the generator and receiver transducers acting on the liquid-filled container under investigation.

FIG. 3 is a schematic representation of the top view of the apparatus of the present invention, illustrating the transmitter and receiver elements acting on the liquid-filled container under investigation. In the drawings which follow, similar or identical structure is labeled with identical callouts. Shown are transmitting element, 10, which includes a conical-shaped, stainless-steel wear plate, 12, a neodymium-boron-iron disk magnet, 14, and piezoelectric transducer, 16, mounted in holding block 18, and receiving element, 20, which includes a conical-shaped stainless-steel wear plate, 22, a neodymium-boron-iron disk magnet, 24, and piezoelectric transducer, 26, mounted in holding block 28. Electrical connections, 30, and 32, which pass through blocks 18 and 28, allow electrical signals to be delivered to and received from piezoelectric transducers 16 and 26, respectively. Angular adjustment joint, 34, permits contact between transmitting and receiving elements, 10 and 20, and the wall, 36, of the container under investigation for curved surfaces. The actual separation between the transmitting and receiving elements is not critical. However, higher separation provides better measurement sensitivity. For a 55-gallon drum, a separation of 2-cm is sufficient, and the two transducers are disposed approximately parallel to the surface of the liquid whose level is to be determined. In thin metal containers, the effect of the liquid on the propagation speed is more pronounced. Thus, a smaller separation would be adequate. For larger containers with thick shells, larger separations are mandated. The size of the piezoelectric transducers is not critical. For small containers, small transducers may be employed. For 55-gallon drums, transducers having 1-cm diameter have been shown to be adequate.

Two methods may be used to ensure physical contact between the transducers and the container surface. Where the container shell is magnetic disk magnets may be employed to control coupling. In other situations, small spheres may be used for sliding the transducers over most surfaces. In both cases, excellent physical coupling may be achieved.

In the practice of the present invention, a tone burst having between 5 and 20 cycles of a fixed sine-wave frequency is applied to transmitting element, 10, which generates a burst of waves in container shell, 36. If the sine-wave frequency is too low, then the duration of the burst may be long enough that reflections from container edges may interfere. That is, the container geometry restricts the lower frequency range employable. Receiving element 20, detects the amplitude of the generated waves and the propagation time between the transducers is determined by measuring the phase difference between the transmitted waveform and the detected waveform. The transmitter/receiver pair is moved in a direction perpendicular to the expected plane of the liquid/gas interface, which interface is detected when a large change in the phase difference occurs. The transmitter/receiver pair is disposed substantially parallel to the liquid surface and perpendicular to the direction of motion of the pair.

Phase measurements are quite accurate, simple and, in most situations, independent of the amplitude of the received signal. A short tone burst is used in order to distinguish the received signal from reflected signals from other parts of the container; for example, the perimeter thereof.

Figure 4:
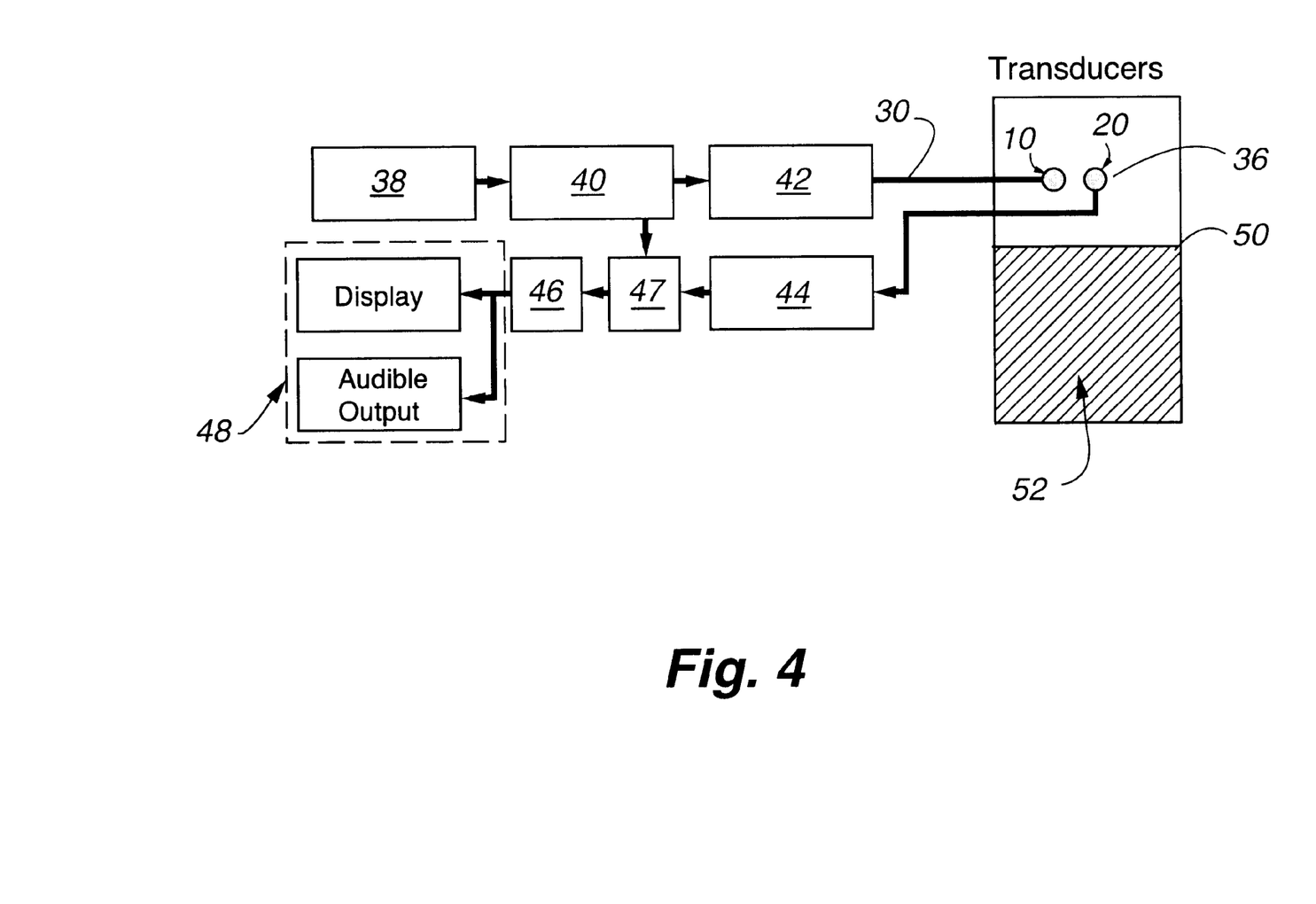
FIG. 4 is a schematic representation of a sample electronics instrumentation suitable for practicing the method of the present invention.

FIG. 4 is a schematic representation of sample electronics instrumentation suitable for practicing the method of the present invention. Sine-wave generator, 38, generates a chosen acoustic frequency between 20 and 100 kHz for the present applications. Burst gating device, 40, generates a burst output of a few cycles of the generated carrier frequency at a chosen rate. The rate is chosen between 20 and 100 Hz, such that any resonance mode excitation in the container has time to die down. The signal level of the burst output is controlled by amplitude control circuit, 42. The output from amplitude control circuit, 42, which may actually be part of sine-wave generator, 38, is applied to piezoelectric element, 16, through electrical connection, 30. Transducer holders, 18 and 28, are gently pressed against container wall, 36, or magnetically coupled. Bending waves in the container shell are thereby excited.

Receiving element, 20, detects this excitation which is amplified by automatic gain control, 44, which also maintains a constant output level. This greatly assists the phase-detection process using phase detector, 46, since the act of sliding the transducers along the container wall changes the degree of physical coupling therewith, making the detected signal amplitude fluctuate. A time gating circuit, 47, may be included after automatic gain control, 44, in order to extract a portion of the detected waveform which overlaps with the transmitted signal and to reject any signal either prior or subsequent to it. In this manner, transients and spurious signals from reflections originating from container edges and the like may be eliminated. Display circuitry, 48, may be digital or analog. For rapid liquid-level detection, an audible alarm may be employed. Whenever level, 50, above liquid, 52, is detected, the alarm would sound.

EXAMPLE 2

Figure 5:
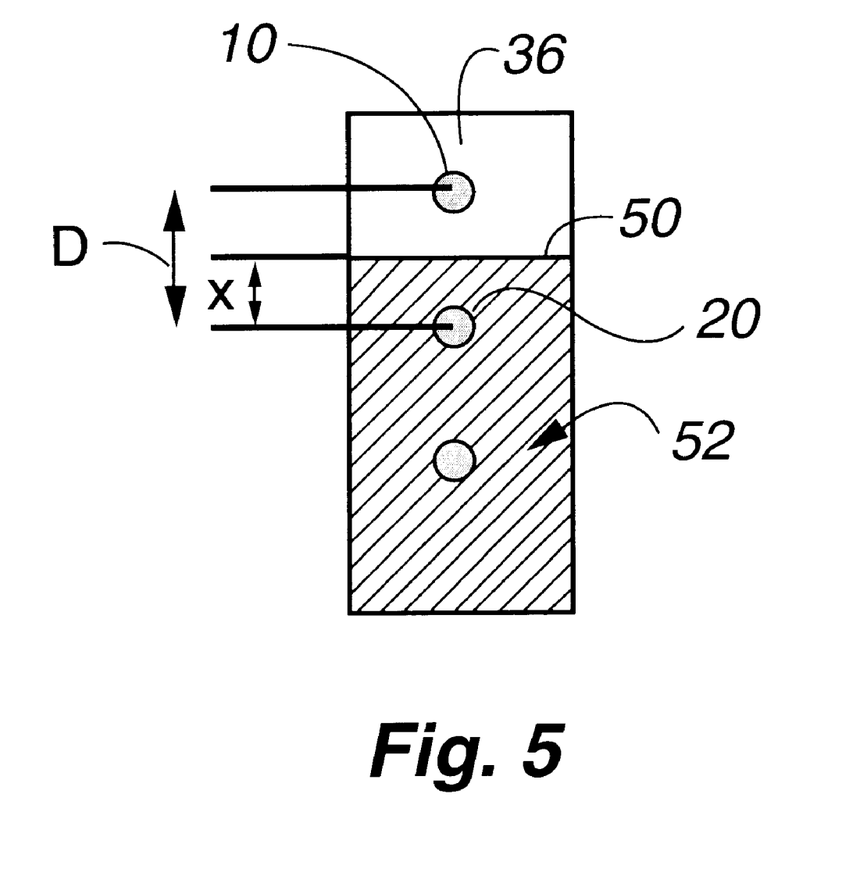
FIG. 5 is a schematic representation of the application of the method of the present invention to the continuous monitoring of liquid levels.

In process control situations, one needs to monitor and control the density of liquids inside reactor vessels at a prescribed level. The present invention may provide appropriate feedback information to controller systems by making continuous measurements of density changes. Often, there is no opportunity for an operator to be present to move the transducers along the surface of the container wall in order to detect the liquid level. In the situation where only changes in the liquid level rather than the position of the liquid level itself are to be measured, continuous-wave excitation may be employed. In this case the transducers need not be moved, and extraneous reflections remain constant while the observed change in phase is due to the variation in the liquid level. The transducers may be positioned such that one transducer is above the liquid level and one is below, such that the line between them is approximately perpendicular to the surface of the liquid, as is illustrated in FIG. 5 hereof. The separation between the transducers should be such that it covers the entire expected range of liquid levels, and it does not matter which of the transducers is the transmitter and which is the receiver. The only other limitation on the spacing is that the phase shift remains within 360°, since phase shifts greater than this result in phase wrapping, potentially incorrect measurements, and interference caused by reflections from the edges, top and bottom of the container. In the anticipated arrangement, part of the excited flexural wave propagates through a portion of the metal wall that has liquid in contact therewith, and the remainder has air against it. Only the transit time between the signals is measured by the present technique.

Assume that the total propagation time is t for the bending wave signal to travel distance, D, between transducers, 10 and 20, with the bending wave traveling at a velocity, $C_L$, for a distance, x, between transducer, 20, and surface, 50, of liquid, 52, and at a velocity, $C_A$, above the liquid for the remainder of the distance, D−x. Then the time for a signal to reach from the transmitting transducer to the receiving transducer is given by:

$$t = \frac{x}{C_L} + \frac{D-x}{C_A} = \left(\frac{1}{C_L} - \frac{1}{C_A}\right) \cdot x + \frac{D}{C_A}. \quad (4)$$

Figure 6:
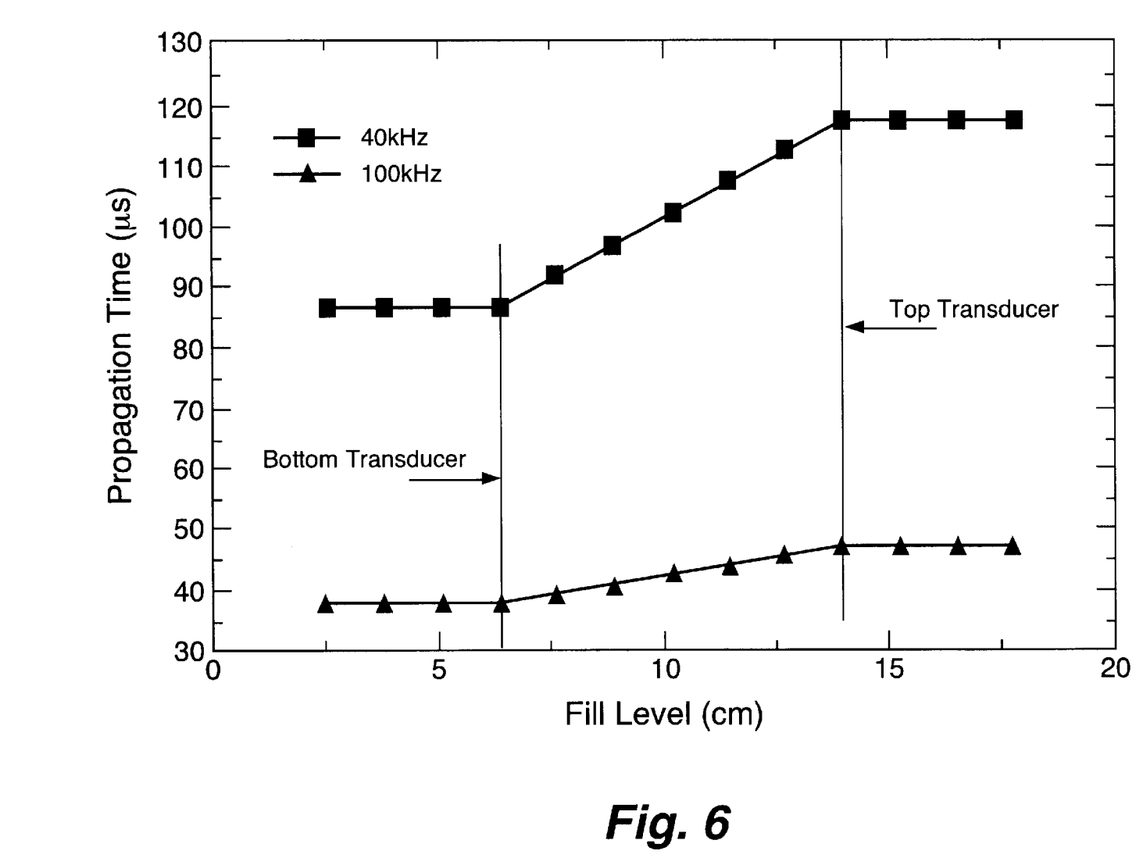
FIG. 6 shows continuous liquid-level measurement experimental data taken for water at two applied frequencies and illustrates that the liquid level may readily be monitored.

For a given container, $C_L$ and $C_A$ are known, and the separation distance between the transducers is fixed. It is seen that the propagation time, t, is linearly related to the liquid level through x. This time can be determined through a phase difference measurement. FIG. 6 illustrates experimental data for a continuous liquid-level measurement for a tank of water at two applied frequencies. Measurements were performed in a steel container having a diameter of −17 cm, a height of −20 cm, and a wall thickness of −0.025 cm. The vertically placed transducers were separated by 7.5 cm, and the water level was changed from above the top transducer, 10, to below the bottom transducer, 20. The tone-burst frequencies were 40 kHz (solid squares) and 100 kHz (solid triangles), and only 3 cycles of each tone burst were used. Measurements were repeated with tone-burst frequencies between 20 kHz and 100 kHz, with all frequencies showing excellent linearity. Measurements were also made using a 55-gallon drum with similar results. The procedure is so sensitive that sloshing at the liquid surface inside the 55-gallon drum as a result of vibrations was readily detected. It should be pointed out that, for tall containers, it might be preferable to use a series of fixed transducers separated by chosen distances. It would be a simple matter to scan all of the transducers to determine which of the pairs straddles the liquid level and to add the height of the highest transducer that is below the liquid level.

EXAMPLE 3

A comparison of the measured phase differences between different drums provides information concerning relative density of liquids present therein. For absolute density measurements, a particular drum must be calibrated, which requires one known liquid, the use of Equations 2 or 3, above, and measurements both above and below the liquid surface in the container. For absolute density measurements using the tone-burst method, one must avoid extraneous effects due to container edges, etc. However, for relative measurements, continuous sine-wave excitation may be employed. The present invention may also be utilized in situations where multiple layers of liquids coexist by moving the transducers along the container wall in a direction perpendicular to the interfaces, thereby determining the interface positions and the relative densities of the layers. This type of information is useful for chemical waste storage drums since it indicates the degree of chemical degradation. Three liquids of slightly different densities were poured into a metal container (10-cm in diameter, 75-cm high and 0.025-cm wall thickness). The liquids (water, vegetable oil and motor oil) were chosen such that clean interface layers were present. A pair of transducers was vertically moved along the outside surface of the container, and the phase difference between the transmitted signal and the received signal for a 30 kHz tone-burst was monitored. As the transducers crossed the interfaces, the phase abruptly changed. Observed phase differences for the three liquids were 50°±1 for water, 40°±1 for vegetable oil, and 34°±1 for motor oil and are consistent with what would be expected as results from Equations 2 and 3 hereof; that is, higher density liquids generate greater phase differences. Although the exact densities of the oils were not measured, generic values therefor range between 0.9 g/cm$^3$ and 1.0 g/cm$^3$, compared with 1.0 g/cm$^3$ for water. Since the theory is only approximate, density measurement procedures would include calibrating the system for a liquid having a well-known density. Since the present apparatus can resolve a 1° phase shift, the density resolution is approximately 0.01 g/cm$^3$. However, for very thick containers, it is expected that the resolution will drop inversely to the square-root of the thickness.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining the location of the liquid/gas interface of a liquid-containing enclosure, said method comprising the steps of:

(a) applying an acoustic sine wave burst having a chosen frequency to a wall of the enclosure which is disposed approximately perpendicular to the liquid/gas interface, establishing thereby a flexural wave in the wall;

(b) detecting the flexural wave generated in the wall at a point on the wall nearby to the location of application of the sine wave burst and in a direction substantially parallel to the liquid/gas interface therefrom; and (c) measuring the phase difference between the sine wave burst and the detected flexural wave; whereby the location of the liquid/gas interface is determined when a change in the magnitude of the phase difference is observed.

2. The method for determining the location of the liquid/gas interface of a liquid-containing enclosure as described in claim 1, further comprising the step of moving the location of application of the sine wave burst and the detection of the flexural wave established thereby in a direction substantially perpendicular to the liquid/gas interface.

3. The method for determining the location of the liquid/gas interface of a liquid-containing enclosure as described in claim 1, wherein said step of applying a sine wave burst to the wall of the liquid-containing enclosure and said step of detecting the flexural wave therein are achieved using piezoelectric transducers in contact with the outside of the wall of the liquid-containing enclosure.

4. A method for determining the density of a liquid in a liquid-containing enclosure, said method comprising the steps of:

(a) applying an acoustic sine wave burst having a chosen frequency to a wall of the enclosure at a location on the wall the opposite side of which location is in contact with the liquid, establishing thereby a flexural wave in the wall;

(b) detecting the flexural wave generated in the wall at a point on the wall nearby to the location of application of the sine wave burst; and (c) measuring the phase difference between the sine wave burst and the detected flexural wave; whereby the liquid density is obtained from the magnitude of the phase difference.

5. The method for determining the density of a liquid in a liquid-containing enclosure as described in claim 4, wherein said step of applying a sine wave burst to the wall of the liquid-containing enclosure and said step of detecting the flexural wave therein are achieved using piezoelectric transducers in contact with the outside of the wall of the liquid-containing enclosure.

6. A method for continuously determining the location of the liquid/gas interface of a liquid-containing enclosure, said method comprising the steps of:

(a) applying a sine wave burst of sound having a frequency, that does not correspond to any resonant mode of the enclosure, to a wall of the enclosure which is disposed approximately perpendicular to the liquid/gas interface, establishing thereby a flexural wave in the wall;

(b) detecting the flexural wave generated in the wall at a point on the wall nearby to the location of application of the sine wave burst and in a direction substantially perpendicular to the liquid/gas interface therefrom, the location of application of the sine wave burst of sound and the location of detecting the flexural wave being located on opposite sides of the liquid/gas interface; and (c) measuring the phase difference between the sine wave burst and the detected flexural wave; whereby the location of the liquid/gas interface is determined by the magnitude of the phase difference.

* * * * *